US011871908B2

(12) United States Patent
Berbee et al.

(10) Patent No.: US 11,871,908 B2
(45) Date of Patent: Jan. 16, 2024

(54) DISPOSABLE SPECULUM FOR DIGITAL OTOSCOPE

(71) Applicant: Wisconsin Alumni Research Foundation, Madison, WI (US)

(72) Inventors: James Berbee, Madison, WI (US); Greg Rebella, Hartland, WI (US); Azita Hamedani, River Hills, WI (US); Patrick Ayerle, Arlington, VA (US); Thomas Hutcheson, IV, Alexandria, VA (US); Ralph Paul, Alexandria, VA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 408 days.

(21) Appl. No.: 17/167,479

(22) Filed: Feb. 4, 2021

(65) Prior Publication Data
US 2021/0161374 A1    Jun. 3, 2021

Related U.S. Application Data

(63) Continuation of application No. 16/281,665, filed on Feb. 21, 2019, now Pat. No. 10,925,478.

(51) Int. Cl.
*A61B 1/227* (2006.01)
*A61B 17/00* (2006.01)

(52) U.S. Cl.
CPC ...... *A61B 1/227* (2013.01); *A61B 2017/0023* (2013.01)

(58) Field of Classification Search
CPC .................. A61B 1/227; A61B 2017/0023

USPC ................................. 600/200; D24/135, 137
See application file for complete search history.

(56) References Cited

U.S. PATENT DOCUMENTS

| 3,840,004 | A | * | 10/1974 | Heine | A61B 1/227 |
| | | | | | 600/200 |
| 4,380,998 | A | * | 4/1983 | Kieffer, III | G01J 5/028 |
| | | | | | 374/E1.013 |
| 4,662,360 | A | * | 5/1987 | O'Hara | G01J 5/02 |
| | | | | | 374/E1.013 |
| 5,179,936 | A | * | 1/1993 | O'Hara | G01J 5/0818 |
| | | | | | 600/203 |
| 5,762,605 | A | | 6/1998 | Cane et al. | |
| 5,919,130 | A | * | 7/1999 | Monroe | A61B 1/042 |
| | | | | | 600/156 |
| 6,106,457 | A | | 8/2000 | Perkins et al. | |
| 6,186,944 | B1 | | 2/2001 | Tsai | |
| 6,450,970 | B1 | | 9/2002 | Mahler et al. | |
| 6,626,825 | B2 | | 9/2003 | Tsai | |
| 7,354,399 | B2 | | 4/2008 | Strom et al. | |

(Continued)

FOREIGN PATENT DOCUMENTS

JP    2007500542    1/2007
WO    2019032689    2/2019

*Primary Examiner* — Eduardo C Robert
*Assistant Examiner* — David C Comstock
(74) *Attorney, Agent, or Firm* — Boyle Fredrickson S.C.

(57) ABSTRACT

A disposable speculum for an otoscope provides a sheath adapted to cover an elongate otoscope probe and providing inwardly extending tabs that are adapted to flex outward when the speculum is inserted over the otoscope to engage corresponding grooves of the otoscope. The inwardly extending tabs provide precise alignment of the speculum with the elongate otoscope probe along an insertion axis to protect a length of the probe.

13 Claims, 4 Drawing Sheets

(56) References Cited

U.S. PATENT DOCUMENTS

| | | |
|---|---|---|
| 8,066,634 B2 | 11/2011 | Andreassen et al. |
| 8,197,403 B2 * | 6/2012 | Strom .................... A61B 1/227 |
| | | 600/193 |
| 9,326,668 B1 | 5/2016 | Berbee et al. |
| 2002/0193665 A1 * | 12/2002 | Jones ................ A61B 1/00105 |
| | | 600/200 |
| 2005/0027169 A1 | 2/2005 | Goldfain et al. |
| 2013/0267783 A1 * | 10/2013 | Davis .................... A61B 1/227 |
| | | 600/199 |
| 2014/0171743 A1 | 6/2014 | Heine et al. |
| 2015/0374208 A1 | 12/2015 | Ruppersberg et al. |
| 2016/0374546 A1 | 12/2016 | Berbee et al. |
| 2018/0000336 A1 | 1/2018 | Gllad-Gilor et al. |
| 2018/0125345 A1 | 5/2018 | Rebella et al. |
| 2018/0125346 A1 | 5/2018 | Shelton et al. |
| 2018/0325501 A1 * | 11/2018 | Robinson ........... A61B 10/0233 |

\* cited by examiner

DISPOSABLE SPECULUM FOR DIGITAL OTOSCOPE

CROSS REFERENCE TO RELATED APPLICATION

This application is a continuation of U.S. patent application Ser. No. 16/281,665 filed Feb. 21, 2019, and hereby incorporated by reference.

BACKGROUND OF THE INVENTION

The present invention relates to a speculum for an otoscope, and in particular, to a speculum that is insertable into an ear canal and surrounds an electronic camera of the otoscope extending along an axis of the speculum to retrieve images of the ear canal.

An otoscope is a medical device allowing a healthcare professional to inspect the ear canal and tympanic membrane (eardrum). A simple otoscope provides for a hollow funnel-shaped speculum whose small end is inserted into the ear canal. The purpose of the funnel shape of the speculum is to provide a visual path to the tympanic membrane and to assist in controlling depth of insertion of the speculum. The speculum also provides a clean barrier between the otoscope and the patient.

Modern otoscopes include an internal source of illumination directed down the speculum axis from a contained battery-operated lamp and may provide a magnifying lens supported outside the ear and aligned with the axis of the speculum to provide an enlarged image of the ear structure being viewed. The speculum may be desirably disposable and normally includes a threaded attachment provided by a short spiral groove on a receiving portion of the otoscope.

More recently, otoscopes have incorporated digital cameras with displays directly on the otoscope for viewing the camera image. An example of these otoscopes is found in U.S. Pat. No. 9,326,668, US patent publication 2016/0374546, US patent publication 2018/0125345, assigned to the present applicant, each of which is hereby incorporated by reference. In such otoscopes, a digital camera may be positioned at the end of a probe that is inserted into the ear.

SUMMARY OF THE INVENTION

The present inventors have recognized that the conventional spiral groove threads used to attach disposable speculums to otoscopes can be suboptimal for digital otoscopes where the axial tip of the speculum must be precisely located to protect the camera without unduly limiting its field-of-view. The spiral engagement of threaded systems can also hamper the use of probes or tools attached to the speculum where precise rotational position and resistance to torque is important.

The present invention provides a disposable speculum for an otoscope that provides a sheath adapted to cover an elongate otoscope probe and providing inwardly extending tabs that are adapted to flex outward when the speculum is inserted over the otoscope to releasably engage corresponding grooves of the otoscope.

Specifically, then, in one embodiment, the invention provides a disposable speculum for an otoscope including a funnel-shaped sheath having a central bore sized to receive an elongate cylindrical probe element of the otoscope therein along an axis and having a distal end sized to fit within an ear canal and a proximal end providing radially inwardly extending teeth flexible outwardly to allow the inwardly extending teeth to releasably engage corresponding grooves of the elongate probe element of the otoscope by an outward movement of the teeth.

It is thus a feature of at least one embodiment of the invention to provide an attachment mechanism that facilitates precise rotational position and axial extension of the axial tip of the speculum to protect the axially extending camera therein. The snap on attachment mechanism provides an intuitive sense of rotational positioning compared to screw type speculums where rotational position may be important, such as when the speculum includes a scraper tool.

The teeth may be flanked by axial slots allowing portions of the proximal end holding the teeth to flex outwardly.

It is thus a feature of at least one embodiment of the invention to provide an engagement mechanism that does not require rotation of the speculum during attachment.

The teeth may have front faces facing toward the distal end and that extend inwardly perpendicular to the axis or canted toward the distal end as one moves inwardly along the front faces.

It is thus a feature of at least one embodiment of the invention to provide teeth that resist axial dislodgement after the teeth engage the corresponding grooves.

Three teeth may be equally spaced at 120° about the axis.

It is thus a feature of at least one embodiment of the invention to provide an attachment mechanism that better resists two dimensions of torsion across the insertion axis and perpendicular to an axis of the probe.

The circumferentially opposed ends of the teeth may provide at least one inwardly sloping wall as one moves radially inwardly along the tooth.

It is thus a feature of at least one embodiment of the invention to decrease contact pressure between teeth and sloped walls of the grooves of the otoscope when the speculum is rotated for release and disposal.

The proximal end may provide a circular rim and the axial slots extend through the rim.

It is thus a feature of at least one embodiment of the invention to provide good outward flexibility of the teeth with simple injection molding techniques.

The proximal end may include a cylindrical portion abutting and supporting the cylindrical probe element. The speculum may further include a tapered portion beyond the cylindrical portion.

It is thus a feature of at least one embodiment of the invention to maximize camera support while reducing tip width required for insertion into the inner ear.

The speculum may further include radially outwardly extending fins rotationally aligned with the teeth.

It is thus a feature of at least one embodiment of the invention to place rotational force directly over the teeth for improved release of the teeth during rotation of the speculum and provide controlled stiffness of flex independent of thickness of the speculum wall.

The sheath may be a thermoplastic material.

It is thus a feature of at least one embodiment of the invention to provide a speculum that is easy to manufacture and thus inexpensive to be disposable for improved safety.

The sheath may be light absorbing.

It is thus a feature of at least one embodiment of the invention to prevent unwanted light leakage into the sheath that may affect the camera images.

The sheath may further include an otoscope housing adapted for support by a hand of a healthcare professional with the housing in an inspection position adjacent to an outer ear of a patient wherein the elongate cylindrical probe element has a proximal end supported by the housing so that a distal end of the elongate cylindrical probe element may extend along the axis into the ear canal; and an otoscope electronic camera supported by a distal end of the elongate cylindrical probe element for viewing into the ear canal when the distal end of the elongate cylindrical probe element is positioned in the ear canal of the outer ear.

It is thus a feature of at least one embodiment of the invention to install the speculum over an otoscope desiring extension of a camera tip into the ear canal.

The corresponding grooves may be radially spaced at 120° about the axis.

It is thus a feature of at least one embodiment of the invention to align the teeth with the grooves by slight (less than a quarter turn) rotation of the speculum.

The corresponding grooves may include a ramp surface.

It is thus a feature of at least one embodiment of the invention to allow for disengagement of the speculum by rotation of the speculum followed by separation of the speculum and otoscope along the axis.

The corresponding grooves may include a front perpendicular face.

It is thus a feature of at least one embodiment of the invention to provide abutment of the teeth against the front face of the groove to resist dislodgement of the speculum.

A distance between a distal end of the sheath and a distal end of the elongate probe element may be approximately 1 mm to 2 mm.

It is thus a feature of at least one embodiment of the invention to provide fixed axial alignment of the speculum extending over the fragile axially extending camera.

In an alternative embodiment, the present invention provides method of using a disposable speculum for an otoscope including the following steps: providing a funnel-shaped sheath having a central bore sized to receive an elongate cylindrical probe element of the otoscope therein along an axis and having a distal end sized to fit within an ear canal and a proximal end providing radially inwardly extending teeth allowing the teeth to flex outwardly to allow the inwardly extending teeth to releasably engage corresponding grooves of the elongate probe element of the otoscope by an outward movement of the teeth; and inserting the sheath into the ear canal.

These particular objects and advantages may apply to only some embodiments falling within the claims and thus do not define the scope of the invention.

DETAILED DESCRIPTION OF THE PREFERRED EMBODIMENT

Figure 1:
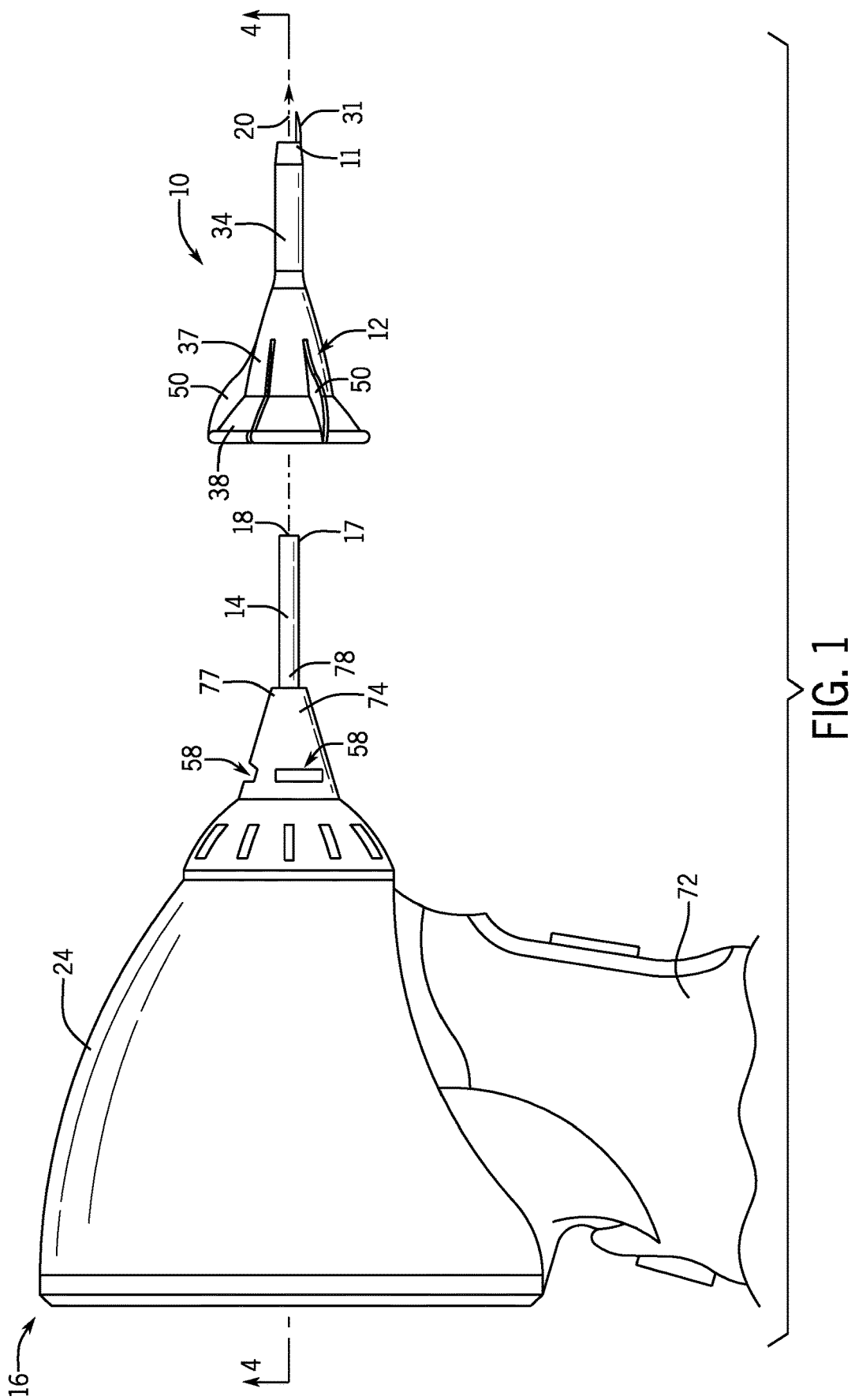
FIG. 1 is a side elevation view of a disposable speculum constructed according to the present invention being inserted onto an otoscope along an insertion axis.

Referring initially to FIG. 1, a removable speculum 10 of the present invention may provide a protective sheath 12 that fits over a cylindrical probe 14 of an otoscope 16 extending along an insertion axis 20 that aligns with the ear canal when the otoscope 16 is used. The otoscope 16 may support on its distal probe tip 17 a front facing electronic camera 18 for acquiring multi-pixel, three-color images in a field of view directed along a speculum axis 22. An otoscope 16 suitable for use with the present invention is described in U.S. Pat. No. 9,326,668, US patent publication 2016/0374546, and US patent publication 2018/0125345, each of which is hereby incorporated by reference.

The removable speculum 10 is attached to the otoscope 16 by a snap lock engagement between the protective sheath 12 and the otoscope 16 supporting the cylindrical probe 14 and electronic camera 18 as further described below.

Figure 2:
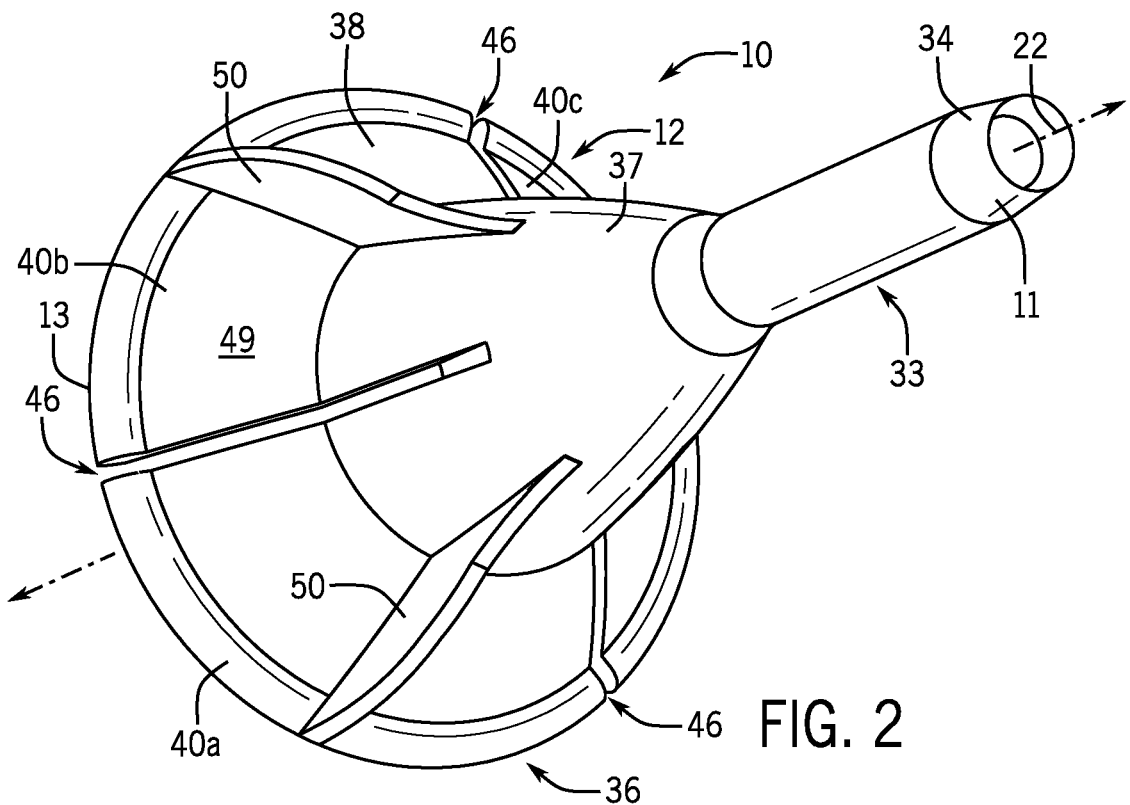
FIG. 2 is a perspective view of an exterior of the disposable speculum of FIG. 1 providing a sheath presenting a flexing collar tapering to a cylindrical tube.

Referring now to FIG. 2, the protective sheath 12 of the removable speculum 10 may be in the form of a hollow trumpet with a central bore extending along the speculum axis 22 and surrounded by the outer sheath 12. The outer sheath 12 is generally radially symmetric at 120 degrees of rotation with progressively increasing amounts of outward flaring along the speculum axis 22 as the sheath 12 flares upward from a distal speculum tip 11 to a circular, outer proximal rim 13 attached to the otoscope 16. An outer diameter of the outer sheath 12 may progressively increase from approximately 2-3 mm of the distal speculum tip 11 to approximately 18-19 mm of the outer proximal rim 13, or progressively increase by 6 to 10 times its minimum diameter.

The outer sheath 12 may be constructed of a non-elastomeric thermoplastic by injection molding. The rigid material of the protective sheath 12 allows the speculum 10 to easily slide over the cylindrical probe 14 without the resistance that might be expected, for example, if the material were an elastomer. The rigid material of the protective sheath 12 also serve to support and protect the relatively fragile cylindrical probe 14 and electronic camera 18. The speculum 10 may be opaque and may be light absorbing, such as black in color, to minimize light leakage into the sheath 12.

A distal portion 33 of the protective sheath 12 extending into the ear canal may provide an elongate tube 34 having a central bore extending along the speculum axis 22, with an inner diameter, measured in a plane perpendicular to speculum axis 22, of approximately 2-3 mm and less than 3 mm and desirably less than 2.3 mm. It is intended that the tube 34 be sized with an outer diameter that is smaller than the ear canal so that it may be inserted therein comfortably, for example, approximately 2-3 mm and less than 3 mm and desirably less than 2.4 mm. The outer diameter of the tube 34 may be minimized to allow for insertion of the tube 34 into smaller sized ear canals, for example, those of toddlers and infants which may be as small as 3 to 4 mm in diameter. A length of the tube 34 may be approximately 8-12 mm and at least 8 mm to allow the protective sheath 12 to extend past minor obstructions, such as normally present earwax, but allow passage of the held electronic camera 18 proximate the ear drum to allow for imaging of the ear drum of the ear.

In certain embodiments, the tube 34 may be cylindrical with a constant inner diameter closely matching the outer diameter of the cylindrical probe 14 for good support, although the tube 34 may also be slightly tapered over this length, for example, tapering toward the narrowed distal speculum tip 11.

The tube 34 is open at the distal speculum tip 11 to allow the held electronic camera 18 to be exposed along the speculum axis 22. The distal speculum tip 11 may support a probe or a tool, for example, a scoop 31 assisting with the removal of ear wax. The scoop 31 extends from the distal speculum tip 11 along the axis 22, and is upwardly concave toward the axis 22.

A proximal portion 36 of the protective sheath 12 may take the form of a funnel 37 having a central bore flaring outwardly from the tube 34 and extending to an increasingly flaring integrally molded collar 38 coupling the otoscope 16. A diameter of a distal end of the funnel 37, measured in a plane perpendicular to the speculum axis 22, may be approximately 2-3 mm, and a diameter of a proximal end of the funnel 37, extending from the distal end of the funnel 37 along the speculum axis 22 by at least 12 mm, may be 9-10 mm. The funnel 37 may be flared outwardly toward the integrally molded collar 38 of the protective sheath 12 at approximately 15-20 degrees from the speculum axis 22 and approximately 18 degrees from the speculum axis 22. The increased diameter of the funnel 37 compared to the narrow tube 34 may assist in controlling the insertion depth of the speculum 10 such that the proximal portion 36 can only extend partially into the ear canal 21 to prevent the distal tube 34 from extending too deeply into the ear canal 21 which would risk damaging or puncturing the ear drum.

The funnel 37 expands outwardly to the increasingly flaring integrally molded collar 38 which is engageable over a head portion 24 of the otoscope 16 to be secured thereon. The collar 38 may take a similar conical shape, flaring outwardly toward the proximal end of the protective sheath 12 at approximately 40-45 degrees from the speculum axis 22 and approximately 45 degrees from the speculum axis 22, in a non-flexed state, providing a greater diameter bore for receiving the head portion 24 of the otoscope 16. A diameter of a distal end of the collar 38, measured in a plane perpendicular to the speculum axis 22, may be approximately 9-10 mm, and a diameter of a proximal end of the collar 38, extending from the distal end of the collar 38 along the speculum axis 22 by at least 3 mm, may be 18-19 mm.

The proximal portion 36 of the protective sheath 12 may provide flexing segments 40 formed by axial slots 46 extending along speculum axis 22 and separating the proximal portion 36 into cantilevered sections that are flexible outwardly and/or inwardly by a distance of approximately 0.1-0.5 mm, and at least 0.1 mm, away from and/or toward the speculum axis 22 at its proximal rim 13. The longitudinally extending slots 46 may be approximately 0.5-1 mm wide and at least 0.5 mm wide and may extend through the proximal rim 13 toward the distal portion 34 a length of at least 8 mm, or at least one-third the length of the protective sheath 12.

In one embodiment the collar 38 may include three equally spaced slots 46 positioned approximately 120 degrees apart about the speculum axis 22 of the proximal portion 36 and forming three cantilevered segments 40a, 40b, 40c supported at a distal end by the protective sheath 12 and detached on left and right sides by the slots 46 and at the proximal rim 13 to allow for outward and/or inward flexure of the segments 40a, 40b, 40c away from and/or toward the speculum axis 22. Each of the segments 40a, 40b, 40c may be independently flexed, however, equal outward/inward forces on segments 40a, 40b, 40c will generally result in substantially equal outward/inward flexure of each segment 40a, 40b, 40c.

An exterior surface 49 of the proximal portion 36 of the protective sheath 12 may support at least one outwardly protruding fin 50 extending from the protective sheath 12. The at least one outwardly protruding fin 50 may generally span between the funnel 37 and the collar 38 to form a generally triangular tab for finger twisting of the protective sheath 12 by a healthcare professional without the need for additional tools. In one embodiment, the proximal portion 36 may carry three equally spaced fins 50 spaced approximately 120 degrees apart about the speculum axis 22 and generally radially centered between the three equally spaced slots 46 described above.

Figure 3:
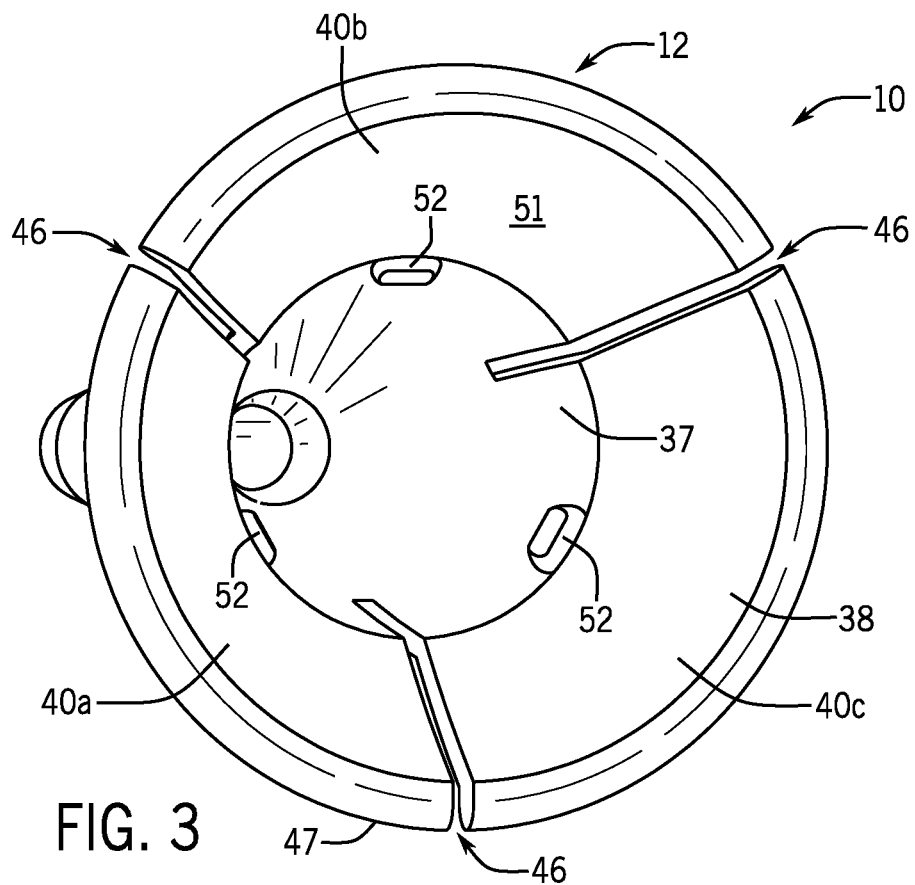
FIG. 3 is a perspective view of an interior of the disposable speculum of FIG. 2 showing multiple teeth flexing outwardly with the flexing collar.

Referring to FIG. 3, an interior surface 51 of the proximal portion 36 may support at least one radially inwardly projecting tooth 52 engaging the inserted head portion 24 of the fully installed otoscope 16. The tooth 52 may take the shape of an oval, oblong or rectangular projection extending from the interior surface 51 toward the speculum axis 22 and having generally rounded outer edges allowing for a sliding or rolling transition of the tooth 52 into and out of a corresponding groove 58 of the otoscope 16. The tooth 52 may be at least 1 mm in width, 3 mm in length, and 0.1 mm in depth. The tooth 52 may be oriented so that a longest dimension of the tooth 52 extends along a circumference of the protective sheath 12 while the shortest dimension of the tooth 52 extends along the speculum axis 22.

Figure 5:
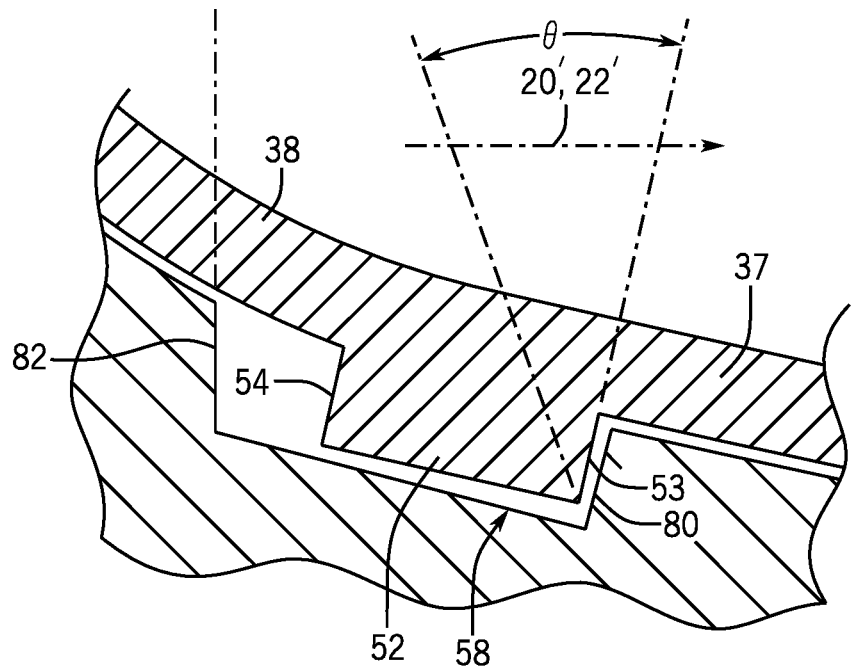
FIG. 5 is an enlarged cross-sectional view similar to FIG. 4 showing a tooth received into a groove of the otoscope having substantially perpendicular side walls.
Figure 6:
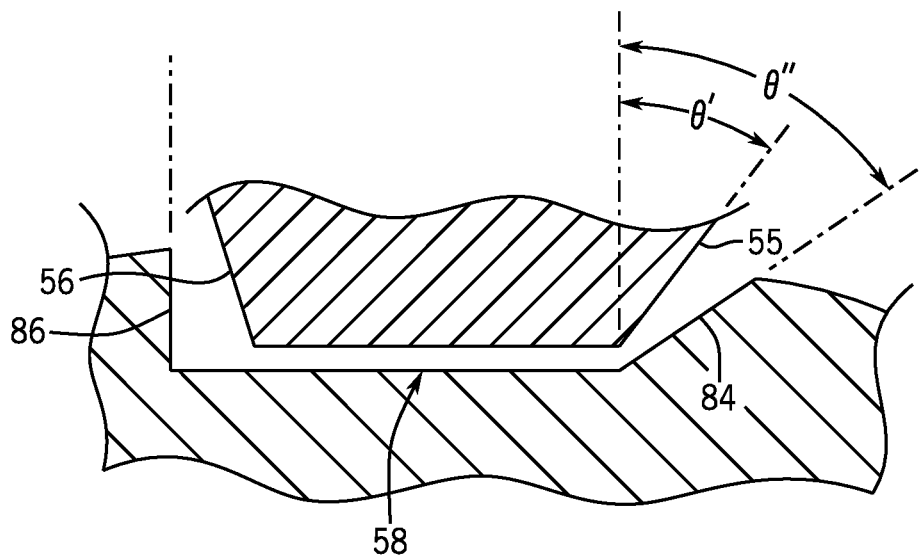
FIG. 6 is an enlarged cross-sectional view, along a vertical plane along lines 6-6 of FIG. 4, perpendicular to the insertion axis of the otoscope showing the tooth received into the groove of the otoscope having at least one ramped side wall.

Turning briefly to FIGS. 5 and 6, each tooth 52 may have a front face 53 facing toward a distal end of the protective sheath 12 that is substantially perpendicular to the speculum axis 22 (axis 22' running parallel to axis 22), as shown, or may also be canted toward the speculum axis 22 as one moves inwardly along the front face 53, and thus oriented to abut the front wall of the groove 58 to prevent removal of the tooth 52 from the groove 58 in a forward direction. A rear face 54 of the tooth 52 may be substantially perpendicular to the speculum axis 22, as shown, or may be canted toward the speculum axis 22 as one moves outwardly along the front face 53, and thus oriented to abut the rear wall of the groove 58 to prevent removal of the tooth 52 from the groove 58 in a rearward direction. Side faces 55, 56 of the tooth 52 may be canted away from the speculum axis 22 as one moves inwardly along the front face 53, as shown, but may also be canted toward the speculum axis 22 as one moves inwardly along the front face 53, or may be substantially perpendicular to the speculum axis 22, and thus oriented to assist with moving the tooth 52 up a ramp of the groove 58. In one embodiment, an interior surface 51 of each section 40a, 40b, 40c may support a single tooth 52. The teeth 52 may be generally centered within each section 40a, 40b, 40c, between the three equally spaced slots 46, and positioned toward the proximal end of funnel 37. The teeth 52 may be rotationally aligned with the outwardly extending fins 50.

Figure 4:
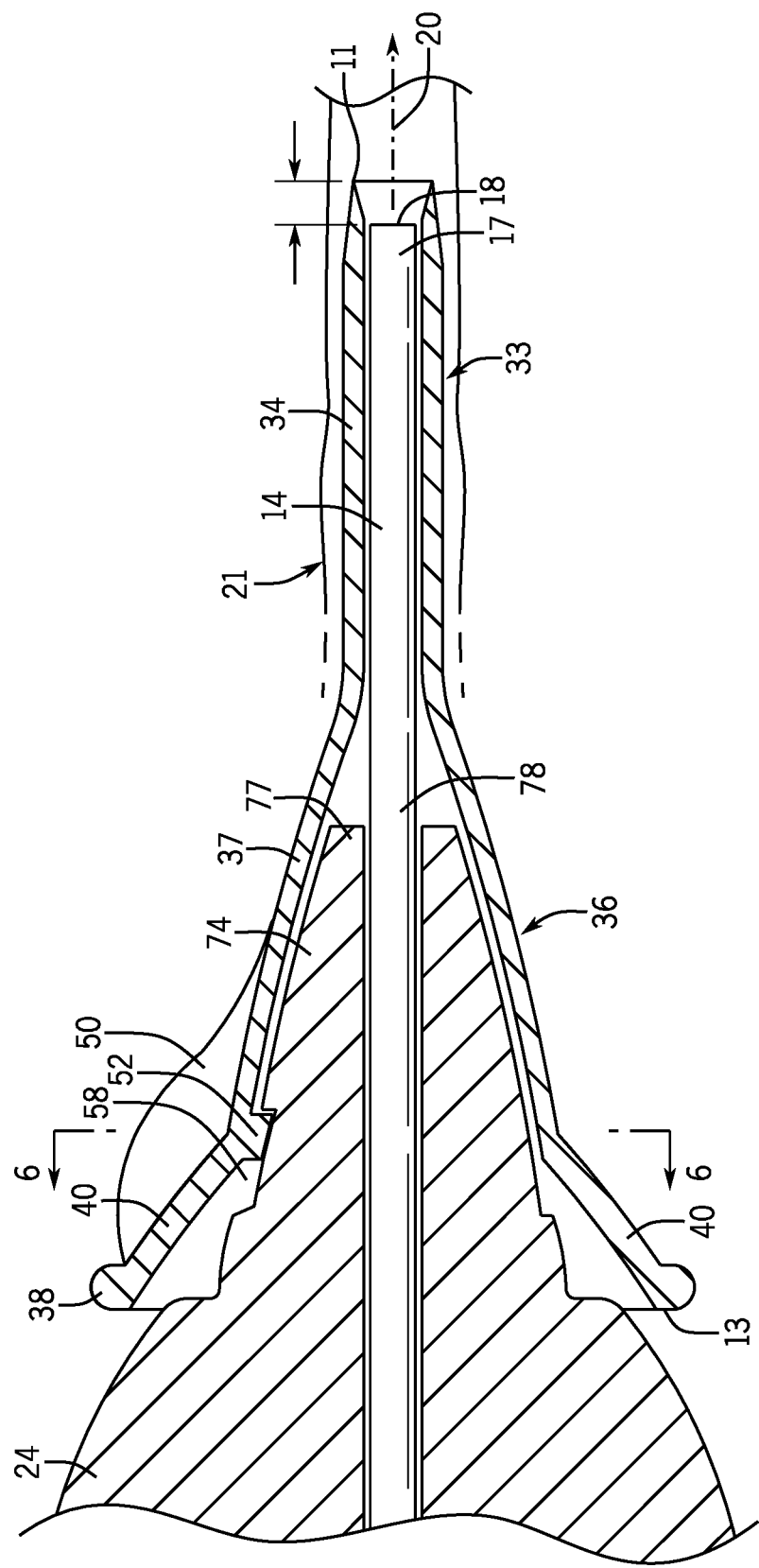
FIG. 4 is a cross-sectional view, along a vertical plane along lines 4-4 of FIG. 1, through the speculum and assembled otoscope of FIG. 1.

Referring now to FIGS. 1 and 4, the removable speculum 10 may slide over an otoscope 16 generally providing a housing having a head portion 24 held up by a detachable grip portion 72. The grip portion 72 is sized to be grasped by the hand of a healthcare professional in the manner of a conventional otoscope with the grip portion 72 extending generally upward from the healthcare professional's hand to the head portion 24.

The head portion 24 of the otoscope 16 may take the shape of a circular cone tapering to a front end defined by a circular tip supporting a frustoconical mounting boss 74. A distal end 77 of the frustoconical mounting boss 74 of the head portion 24 of the otoscope 16 supports the extension of the cylindrical probe 14 having a proximal end 78 supported by the head portion 24 and distal end or tip 17 that extends along the axis 20 of the ear canal 21. The cylindrical probe 14 may extend approximately a length of 8-10 mm and at least 8 mm, to allow the front facing electronic camera 18 at the distal probe tip 17 to reach a desired depth within the ear canal 21. The distal tip 17 of the cylindrical probe 14 supports the electronic camera 18 for viewing into the ear canal 21 and communicating with an electronic display displaying the otoscope image from the electronic camera 18 and is positioned at the distal tip 17 of the cylindrical probe 14 along the axis 20 and centered along the axis 20 as understood in the art. The electronic camera 18 may, for example, be a self-contained charge coupled device (CCD) camera such as is commercially available providing, for example, a measurement area of 1.4 mm diagonal and 62,500 pixels.

An outer rim of the frustoconical mounting boss 74 may provide grooves 58 therein and corresponding with the teeth 52 of the removable speculum 10. The grooves 58 of the otoscope 16 may be generally rectangular holes approximately 1 to 2 mm in width, 3 to 4 mm in length, and 0.1 to 0.5 mm in depth. In one embodiment, the cylindrical mounting boss 74 may support three equally spaced grooves 58 spaced approximately 120 degrees apart about axis 20 whereby a greatest dimension of the rectangle extends along a circumference of the cylindrical mounting boss 74 and a shortest dimension of the rectangle extends along axis 20.

Referring now to FIG. 5, the rectangular grooves 58 may provide front and rear substantially perpendicular side walls 80, 82 (to axis 20' parallel to axis 20), respectively, preventing the teeth 52 from being removed from the grooves 58 in forward and rear directions along the axis 20. In this manner, the removable speculum 10 cannot be easily removed by the healthcare professional and is secured to the otoscope 16 once installed.

Referring now to FIG. 6, the rectangular grooves 58 may provide lateral side walls 84, 86 whereby at least one of the side walls 84, 86 is angled to provide a ramp in which the tooth 52 may slide or ride up the angled side wall 84, 86 and become disengaged from the groove 58 when the removable speculum 10 is rotated in at least one of a clockwise or counterclockwise direction. The angulation of at least one of the sidewalls 84, 86 may be at least 45 degrees from perpendicular and at least 45 degrees. It is understood that one or both of the lateral side walls 84, 86 may be angled to provide an exit ramp for the tooth 52. In one embodiment, one lateral side wall 84 is angled while the opposite side wall 86 extends substantially perpendicular to the floor of the groove 58. In this respect, twisting motion in one direction (toward the angled side wall 84) will allow for the removal of the removable speculum 10 from the head portion 24 of the otoscope 16 while twisting motion in the opposite direction will be prevented by the substantially perpendicular side wall 86. In an alternative embodiment, both lateral side walls 84, 86 are angled such that twisting in either clockwise or counterclockwise directions will allow for the removal of the removable speculum 10 from the head portion 24 of the otoscope 16.

Referring again to FIGS. 1, 4 and 5, the removable speculum 10 may be inserted over the cylindrical probe 16 by sliding the speculum 10 rearward along the insertion axis 20 over the cylindrical probe 16 whereby the central bore of the tube 34 holds the cylindrical probe 14 carrying the front facing electronic camera 18 at its tip 17. The segments 40a, 40b, 40c of the removable speculum 10 may flex outward to accommodate the head portion 24 as it is inserted into the speculum 10. The speculum 10 is inserted along axis 20 until the collar 38 extends over the boss 74 of the removable speculum 10. The speculum 10 may not need to be rotated if the teeth 52 are aligned with the grooves 58 when inserted along axis 20 but in some cases may need to be slightly rotated (less than a quarter turn) until the teeth 52 align with the grooves 58 and the removable speculum 10 snaps into place.

Once installed, the axial position of the distal speculum tip 11 of the removable speculum 10 is set so that the distal tip 17 of the cylindrical probe 14 may terminate before the distal tip 11 of the removable speculum 10. In one embodiment, the distance between the distal tip 17 of the cylindrical probe 14 and the distal tip 11 of the removable speculum 10 may be approximately 1-2 mm, or less than 2 mm. The distance between the distal tip 17 of the cylindrical probe 14 and the distal tip 11 of the removable speculum 10 may be set to minimize blinding internal reflection and narrowed field of view of the electronic camera 18 while still protecting the fragile electronic camera 18 from contamination and damage.

Referring again to FIG. 6, an approximately quarter turn twist of the removable speculum 10 slides the tooth 52 along one of the angled side walls 84, 86 while the segments 40a, 40b, 40c of the removable speculum 10 flex outward (at least 0.1 mm) to accommodate the outward movement of the tooth 52. Once the tooth 52 is displaced from the groove 58, forward motion of the removable speculum 10 along the axis 20 allows the removable speculum 10 to be detached from the head portion 24 of the otoscope 16.

As is generally understood, the outer ear of a human patient includes a pinna providing a sound collecting structure. The pinna surrounds the ear canal 21 leading to and terminating at the tympanic membrane or eardrum. A length of the ear canal 21 in an average adult human is approximately 25 mm and the ear canal 21 has an average diameter of approximately 7 mm. A length of the ear canal 21 in an average infant is approximately 5 and the ear canal 21 has an average diameter of approximately 3-4 mm.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. A disposable speculum for an otoscope comprising:
   a funnel-shaped sheath having a central bore sized to receive an elongate cylindrical probe element of the otoscope therein along an axis and having
   a distal end sized to fit within an ear canal and
   a proximal end providing at least one radially inwardly extending tooth flexible outwardly to allow the at least one radially inwardly extending tooth to releasably engage corresponding grooves of the elongate probe element of the otoscope by an outward movement of the at least one radially inwardly extending tooth,
   wherein the at least one radially inwardly extending tooth is spring biased inward to retract against a sloped surface of the otoscope when the speculum is rotated about the axis,
   wherein the distal end of the funnel-shaped sheath includes a cylindrical portion joined to a tapered tip, the distal end having an outer diameter of less than 4 mm.

2. The disposable speculum of claim 1 wherein the at least one radially inwardly extending tooth is engageable with corresponding grooves of the elongate cylindrical probe element of the otoscope and wherein the at least one radially inwardly extending tooth has front faces facing toward the distal end and extending inwardly perpendicular to the axis or canted toward the distal end as one moves inwardly along the front faces.

3. The disposable speculum of claim 1 wherein the at least one radially inwardly extending tooth is engageable with corresponding grooves of the elongate cylindrical probe element of the otoscope and wherein circumferentially opposed ends of the at least one radially inwardly extending tooth provides at least one inwardly sloping wall as one moves radially inwardly along the tooth.

4. The disposable speculum of claim 1 wherein an outer diameter of the distal end is less than 3 mm.

5. A disposable speculum for an otoscope comprising:
   a funnel-shaped sheath having a central bore sized to receive an elongate cylindrical probe element of the otoscope therein along an axis and having
   a distal end sized to fit within an ear canal and
   a proximal end providing inwardly extending teeth engageable with corresponding grooves of the elongate cylindrical probe element of the otoscope
   wherein the inwardly extending teeth include three teeth equally spaced at 120° about the axis,
   wherein the distal end of the funnel-shaped sheath includes a cylindrical portion joined to a tapered tip, the distal end having an outer diameter of less than 4 mm.

6. The disposable speculum of claim 5 wherein the inwardly extending teeth are engageable with corresponding grooves of the elongate cylindrical probe element of the otoscope and wherein the teeth have front faces facing toward the distal end and extending inwardly perpendicular to the axis or canted toward the distal end as one moves inwardly along the front faces.

7. The disposable speculum of claim 5 wherein the inwardly extending teeth are engageable with corresponding grooves of the elongate cylindrical probe element of the otoscope and wherein circumferentially opposed ends of the teeth provide at least one inwardly sloping wall as one moves radially inwardly along the tooth.

8. The disposable speculum of claim 5 wherein an outer diameter of the distal end is less than 3 mm.

9. A disposable speculum for an otoscope comprising:
   a funnel-shaped sheath having a central bore sized to receive an elongate cylindrical probe element of the otoscope therein along an axis and having
   a distal end sized to fit within an ear canal and
   a proximal end providing at least one radially inwardly extending tooth flexible outwardly to allow the at least one radially inwardly extending tooth to releasably engage corresponding grooves of the elongate probe element of the otoscope by an outward movement of the at least one radially inwardly extending tooth and outwardly extending fins extending along the axis a length across a position of the at least one radially inwardly extending tooth along the axis.

10. The disposable speculum of claim 9 wherein the at least one radially inwardly extending tooth is engageable with corresponding grooves of the elongate cylindrical probe element of the otoscope and wherein the at least one radially inwardly extending tooth has front faces facing toward the distal end and extending inwardly perpendicular to the axis or canted toward the distal end as one moves inwardly along the front faces.

11. The disposable speculum of claim 9 wherein the at least one radially inwardly extending tooth is engageable with corresponding grooves of the elongate cylindrical probe element of the otoscope and wherein circumferentially opposed ends of the at least one radially inwardly extending tooth provide at least one inwardly sloping wall as one moves radially inwardly along the tooth.

12. The disposable speculum of claim 9 wherein an outer diameter of the distal end is less than 3 mm.

13. The disposable speculum of claim 9 wherein the outwardly extending fins control insertion depth of the probe to prevent ear drum damage.

* * * * *